US00PP11208P

United States Patent [19]

Tsuji et al.

[11] Patent Number: Plant 11,208

[45] Date of Patent: Feb. 8, 2000

[54] CLINGSTONE PEACH TREE NAMED 'LATE ROSS '

[75] Inventors: Bill H. Tsuji, Parlier; Theodore M. Dejong, Davis; James F. Doyle, Clovis, all of Calif.

[73] Assignee: The Regents of the University of California, Oakland, Calif.

[21] Appl. No.: 09/105,038

[22] Filed: Jun. 26, 1998

[51] Int. Cl.[7] ..... A01H 5/00

[52] U.S. Cl. ..... Plt./197

[58] Field of Search ..... Plt./197

[56] References Cited

U.S. PATENT DOCUMENTS

P.P. 4,863 7/1982 Davis, et al. ..... Plt./197

P.P. 6,230 7/1988 Arakelian, Sr. ..... Plt./197

*Primary Examiner*—Howard J. Locker

*Assistant Examiner*—Wendy A Baker

*Attorney, Agent, or Firm*—Burns, Doane, Swecker & Mathis, L.L.P.

[57] ABSTRACT

A new and distinct cultivar of peach tree (i.e., *Prunus persica*) is provided that originated as a scaffold mutation of unknown causation of the 'Ross' cultivar (U.S. Plant Pat. No. 4,863). The new cultivar forms attractive fruit that is well suited for canning which matures approximately ten days later than that of the parent 'Ross' cultivar. Commonly a distinct red stripe is formed on the suture line of the fruit. All other characteristics of the new cultivar are believed to be substantially identical to those of the 'Ross' cultivar. The later fruit maturity offers fruit growers and canneries more flexibility in the harvesting and canning of the fruit crop through the simultaneous growing of the 'Ross' cultivar and the new cultivar of the present invention without sacrifice of fruit quality.

1 Drawing Sheet

BACKGROUND OF THE INVENTION

The 'Ross' cultivar of clingstone peach is the subject of U.S. Plant Pat. No. 4,863. Such cultivar was the product of a breeding program carried out at the University of California experimental orchard located at Davis, Calif. The 'Ross' cultivar is recognized to possess many attractive attributes, such as productivity, regularity of bearing, uniformity of fruit size, and processed fruit quality, and is being grown primarily by commercial cling peach growers for canning. It currently is believed to be the most heavily planted canning peach in California. The harvest period for the 'Ross' cultivar is currently recognized to substantially coincide with that of older cling peach cultivars, such as 'Carolyn' and 'Monaco' (each non-patented in the United States). However, these older cultivars are known to commonly exhibit less desirable fruit production characteristics than the 'Ross' cultivar.

SUMMARY OF THE INVENTION

The present invention is directed to a new and distinct peach (i.e., *Prunus persica*) cultivar that was discovered during 1994 as a scaffold mutation of unknown causation of the 'Ross' cultivar. The new cultivar while propagated on Nemaguard peach rootstock was found within an orchard planted during 1990 at the Kearney Argricultural Center of the University of California located at Parlier, Calif. Such orchard had been planted primarily to investigate the production characteristics of various high density tree training systems.

At the time of discovery a single tree of the 'Ross' cultivar was found to possess a single late maturing scaffold. The fruit on such branch was observed to be of considerably less maturity than all other fruit formed on such 'Ross' trees. The potential value of such difference in fruit maturity was recognized and the tree was carefully preserved and the fruit which was recognized to be immature at the time of the 'Ross' harvest was left unpicked. The original tree has undergone extensive observation and testing in subsequent years. Had the new cultivar of the present invention not been discovered and preserved it would have been lost to mankind.

The new clingstone peach cultivar of the present invention has been found to exhibit the following combination of characteristics:

(a) forms attractive fruit that matures approximately ten days later than that of the 'Ross' cultivar (U.S. Plant Pat. No. 4,863).

(b) forms a distinct red stripe on the suture line of the mature fruit, and (c) exhibits other characteristics that are believed to be substantially the same as those as the 'Ross' cultivar.

During 1995 the new cultivar was propagated at Davis, Calif., by grafting on peach rootstocks of approximately two years of age. Such propagation bore fruit during 1996 with the first substantial crop occuring in 1997 and has been observed to reproduce true to type in all respects.

Some fruit of the new cultivar from the original scaffold was canned at Davis, Calif., during 1995, and has undergone quality testing. During such testing canned fruit of the new cultivar was awarded high ratings as was the fruit of the 'Ross' cultivar.

Wood of the new cultivar has been subjected to the virus indexing program of Foundation Plant Materials Service, University of California at Davis, Calif. All indices have proven to be negative for viruses.

Since the initial fruit harvest time of the new cultivar generally coincides with the final harvest time for the parent 'Ross' culivar, it is now possible to provide canneries with a continued supply of high quality peaches over an additional two to three week period of the growing season. The canning sequence made possible by the older 'Ross' cultivar and the mutation of the present invention offers fruit growers and canneries more flexibility in the harvesting and canning of the fruit crop through the use of both the old cultivar and the new cultivar without sacrifice in fruit quality. Accordingly, existing canneries located near the growing areas where the 'Ross' cultivar is grown conveniently can process the new cultivar without the need for any substantial additional capital expenditure.

The new cultivar of the present invention has been named 'Late Ross'.

BRIEF DESCRIPTION OF THE PHOTOGRAPH

The accompanying photograph shows specimens of the foliage and fruit of the new cultivar as depicted in color as nearly true as it is possible to make the same in a color illustration of this character. The tree of the new cultivar was grown at the Kearney Agricultural Center of the University of California located at Parlier, Calif. The fruit was near full commercial maturity.

DETAILED DESCRIPTION

The following is a detailed description of the new cultivar obtained from the original scaffold mutation and its progeny during the 1997 growing season. The trees were grown at the Kearney Agricultural Center of the University of California located at Parlier, Calif. Color designations are presented with reference to the "Dictionary of Color" by Maerz and Paul, First Edition (1930).

Botanical classification: *Prunus persica*, cv. 'Late Ross'.

Tree:

*Size.*—Medium. The trees resulting from the asexual propagation of 1995 during the fall of 1997 had a height of approximately 3.6 meters, a breadth of aproximately 3.7 meters across the crown, and commonly possessed approximately five scaffolds.

*Vigor.*—Medium. Produced approximately 0.77 to 0.91 meter of new growth during the 1997 growing season.

*Growth.*—Upright to upright-spreading.

*Hardiness.*—Hardy under typical San Joaquin Valley climatic conditions.

*Production.*—Productive.

*Bearing.*—Regular bearer.

Trunk:

*Size.*—Medium to large. The trunk diameter of the original tree at 10 cm. above the ground is approximately 22 to 24 cm. The scaffold diameters at the base of the scaffolds are approximately 12 cm. and those of the parent 'Ross' cultivar are approximately 10.8 to 11 cm.

*Texture.*—Relatively coarse with substantial scarfskin.

*Color.*—The bark color ranges from brown-grey (15-C-8 Chukker Brown) to more medium brown (8-J-10 Falcon Brown).

*Lenticels.*—Numerous, large, flattened and generally oval-shaped. Typically the lenticels range from approximately 2 to 7 mm. in width at a right angle to the trunk and are approximately 1 to 3 mm. in height. The lenticel surface is light brown in coloration (13-H-8 Bure Brown) and is somewhat calloused.

Branches:

*Size.*—Medium.

*Texture.*—Medium.

*Color.*—Mature shoots are light brown (14-1-8Madura Brown) to darker brown (7-E-11 Trotteur Tan). The current season's shoots are pale light green (18-1-5 Sky Green). The exposed surfaces are commonly tinged rose-red (5-J-9 Bois de Rose). The coloration of the new expanding shoot tips is bright yellow green (17-L-4).

*Lenticels.*—Somewhat linear at a right angle to the shoots, and light in coloration.

*Internode length.*—On current season's hanger shoots the length between nodes commonly is approximately 10 to 25 mm.

Leaves:

*Size.*—Medium to large. Typical length from vigorous current season's growth is approximately 15.7 to 17.7 cm. including the petiole, and typical width is approximately 3.9 to 4.6 cm. The leaf thickness is average.

*Form.*—Lanceolate.

*Apex.*—Acuminate and often curves downward and is twisted sideways.

*Aspect.*—The blade commonly ranges from substantially flat to somewhat folded upwards.

*Color.*—The upper surface is dark green (23-J-6) and the lower surface is a much lighter grey-green (21-H-6). The primary and mid-vein on the under surface is pale yellow-green (17-J-3).

*Margin.*—Crenate and occasionally double crenate. The crenations are relatively large and uniform. The leaf margins commonly range from straight to moderately undulate.

*Petiole.*—Generally medium in size, commonly approximately 8 to 10 mm. in length, approximately 2 mm. in thickness, and pale yellow-green in coloration (17-H-4).

*Glands.*—Small to medium in size, almost always globose, alternate, commonly 1 to 2 on the petiole, often borne on a short stalk, and frequently 0 to 2 additional glands can be observed at the base of the leaf blade. The coloration is shiny light green-yellow (17-K-5) and often with a reddish center.

*Stipules.*—Linear lanceolate in configuration, most are early deciduous, margins are serrate, commonly approximately 6 to 9 mm. in length, and the coloration of young stipules commonly is light green-yellow (17-K-5) with darkening to brownish upon aging.

Fruit:

*Maturity when described.*—Full commercial maturity.

*Picking.*—First pick was Aug. 1, 1997 and last pick was Aug. 6, 1997.

*Season of maturity.*—Approximately ten days later than the 'Ross' cultivar (U.S. Plant Pat. No. 4,863).

*Size.*—Uniform, large. Average axial diameter is approximately 61 to 67 mm., the average suture diameter is approximately 64 to 71 mm., and the average cheek diameter is approximately 65 to 72 mm.

*Form.*—Globose to slightly oblate in lateral aspect, and in the apical aspect varies from globose to slightly oval with a slight elongation of the ventral suture area. Most frequently the fruit is slightly asymmetrical.

*Suture.*—Clearly evident and extends from the fruit base to the apex. Overall the suture is quite shallow, but sometimes deepens within the stem basin and is slightly depressed at the apical end. A slight amount of stitching sometimes is present. The width commonly ranges from 1 to 4 mm. The suture line characteristically is light red (5-K-10 Ember Red) to a darker red (6-L-11 Egyptian Red). Such a distinct red stripe on the suture commonly is absent on the fruit of the parent 'Ross' cultivar and sometimes is there replaced by a red blush at the area of the suture.

*Ventral surface.*—Relatively smooth and only occasionally lipped.

*Base.*—Commonly varies from round to slightly truncate. The base angle commonly is also visible and most frequently is at a right angle to the fruit axis, but occasionally is slightly oblique to the fruit axis.

*Stem cavity.*—Oval, relatively small, commonly approximately 26 to 32 mm. in length, approximately 20 to 29 mm. in width, and approximately 12 to 14 mm. in depth. Some depressions may be present in the cavity shoulder where the fruit was pressed next to a bearing fruit shoot.

*Apex.*—Commonly rounded with a depressed tip.

*Pistil point.*—Most frequently is oblique.

*Stem length.*—Commonly approximately 5 to 6 mm.

*Stem thickness.*—Commonly approximately 3 to 3.5 mm. and usually more thickened at the distal end.

*Stem color.*—Light greenish-yellow (12-L-3 Pyrite Yellow) to slightly more yellowish (11-L-2 Pyrethrum Yellow).

*Skin pubescence.*—Lightly to moderately pubescent, with short, fine greyish pubescence.

*Skin flavor.*—Relatively neutral.

*Skin tenacity.*—Tightly attached to the flesh at commercial maturity.

*Skin tendency to split.*—None observed.

*Skin color.*—A mix of yellow ground color and a red blush with a distinctive red suture line. The red blush can vary from approximately 10 to 50 percent of the skin surface. The blush form includes both washed and striped patterns. The blush coloration commonly ranges from medium red (5-H-10 Rosewood) to dark red (6-L-12 Indian Red) with degrees of shading in between. The red suture line ranges from light red (5-K-10 Ember Red) a darker red (6-L-11 Egyptian Red). The washed areas of red color can be somewhat dappled and speckled in appearance. The ground color ranges from light yellow (9-K-3 Empire Yellow) to a more golden yellow (9-L-6 Golden Glow). The ground color commonly covers approximately 50 to 90 percent of the fruit surface.

*Flesh color.*—Very uniform yellow from skin to stone (9-L-5). A very few short whitish fibers occasionally are present. No red coloration is present under the skin or next to the stone at commercial maturity.

*Flesh texture.*—Firm, very fine textured, and non-melting.

*Ripening.*—Ripens evenly.

*Flavor.*—Very pleasant, mild and well balanced.

*Aroma.*—Pleasant and moderate.

*Eating quality.*—Good.

*Canning quality.*—Very good.

*Stone type.*—Clingstone with flesh connected over the entire stone surface.

*Stone size.*—Medium and commonly ranges from approximately 34 to 38 mm. in length, approximately 25 to 28 mm. in width, and approximately 17 to 22 mm. in thickiness.

*Stone form.*—Sightly obovate and at times approaching oval.

*Stone base.*—Slightly oblique to the stone axis.

*Stone hilum.*—Relatively large and well defined, oval, with a thickened collar, substantially grooved, and present surrounding the hilum scar.

*Stone apex.*—Generally rounded with a short tip.

*Stone sides.*—Somewhat variable, ranging from equal to very slightly unequal.

*Stone surface.*—Pitted and grooved with the pitting being most distinct over the mid-stone surfaces laterally, and the grooves most distinct near the stone base and along the ventral edge.

*Ventral surface.*—Relatively narrow, commonly from 5 to 6 mm. in width at mid-suture. Low wings commonly are present along the entire ventral edge with substantial erosion of the wings over the basal shoulder to the base.

*Dorsal edge.*—Relatively prominent, and deeply grooved from the base to within approximately 5 to 10 mm. of the apex. The apical shoulder is substantially eroded, especially in near proximity to the apex. The ridges subtending the dorsal groove are high and occasionally cross-cut with grooves.

*Stone color.*—When dry, light tan-brown (14-D-9).

*Tendency to split.*—None observed.

Flowers:

*Chilling season.*—Low to medium for growing location. There were approximately 827 chilling hours below 45° F. for the 1996—1997 winter season.

*Buds.*—Medium to large in size, conic in form, plump, slightly appressed to the bearing shoot, and bear pubescent surfaces of a light grey coloration. The exterior bud scale ranges from grey (15-A-6 Beaver Grey) to grey-brown (15-A-8 Winter Leaf Brown) in coloration. The buds are hardy under typical climatic conditions of the San Joaquin Valley. There commonly are one to two floral buds per node and most frequently two floral buds per node.

*Bloom timing.*—Early to midseason in relation to other commercial cling peach cultivars. During 1997 was approximately two days after the parent 'Ross' cultivar. More specifically, the date of the first bloom was Feb. 18$^{th}$ and the date of full bloom was Mar. 5$^{th}$. In comparison, the 'Ross' cultivar exhibited a date of first bloom of Feb. 16$^{th}$ and a date of full bloom of Mar. 3$^{rd}$.

*Size.*—The flower size is large and showy. The fully expanded flower diameter commonly is approximately 28 to 40 mm.

*Bloom quality.*—Commonly abundant throughout the tree.

*Petals.*—The petal size is large and commonly ranges from approximately 17 to 21 mm. in length and from approximately 17 to 20 mm. in width. The petal number is five. The petal form varies from broadly ovate to at times nearly oval. The young petals are light pink (1-C-7 Pink #2) and darken slightly at maturity to (1-E-2). The petal claw is moderately large and truncate in form. The claw color is dark rose-pink (1-J-4 Rose Neyron) and darker than the overall petal. The petal margins vary from moderatly smooth to somewhat ruffled. The petal apices are variable, most frequently rounded and are somewhat raised at times.

*Pedicel.*—Quite short and commonly exhibits a length of approximately 1 to 1.5 mm. and a thickness of approximately 1 to 1.5 mm. The coloration is bright green (17-L-6) and the surface is glabrous.

*Nectaries.*—Bright orange (9-C-11) and becoming slightly darker at maturity.

*Calyx.*—Glabrous and quite rugose, and the coloration is light maroon (5-J-4) with areas of green (19-L-2) Jewel Green) especially basally, and darkening to intense maroon (6-J-5) Rubaiyat).

*Sepals.*—Highly pubescent with long greyish pubescence, average in size, conic in form, and dark maroon (6-J-4 to 6-J-5) in coloration.

*Anthers.*—Average in size, dark red dorsally (5-L-11 Brickdust) and tan-red ventrally (4-A-10 Woodland Rose) with red streaking (5-K-9 Rosevale Red) on each side of the filament attachment.

*Stamens.*—Varible in length and commonly range from approximately 11 to 15 mm. in length. Frequently extend well above the pistil. The filaments are very pale pink when young (1-C-1) and become dark maroon (3-J-5) with advancing maturity.

*Pollen.*—Abundant yellow-gold (10-K-5) in coloration.

*Pistil.*—Very pubescent basally over the ovary, and less so near the stigma and over the upper style area. The length commonly is approximately 12 to 15 mm. including the ovary. The coloration basally is pale green (17-J-3) and a paler green (17-J-1) over the upper style area.

Major use: Canning.

Keeping quality: Good.

Resistance to insects and diseases: Average.

We claim:

1. A new and distinct cultivar of peach tree exhibiting the following combination of characteristics:

(a) forms attractive fruit that matures approximately ten days later than that of the 'Ross' cultivar (U.S. Plant Pat. No. 4,863), (b) forms a distinct red stripe on the suture line of the mature fruit, and (c) exhibits other characteristics that are believed to be substantially the same as those as the 'Ross' cultivar;

substantially as illustrated and described.

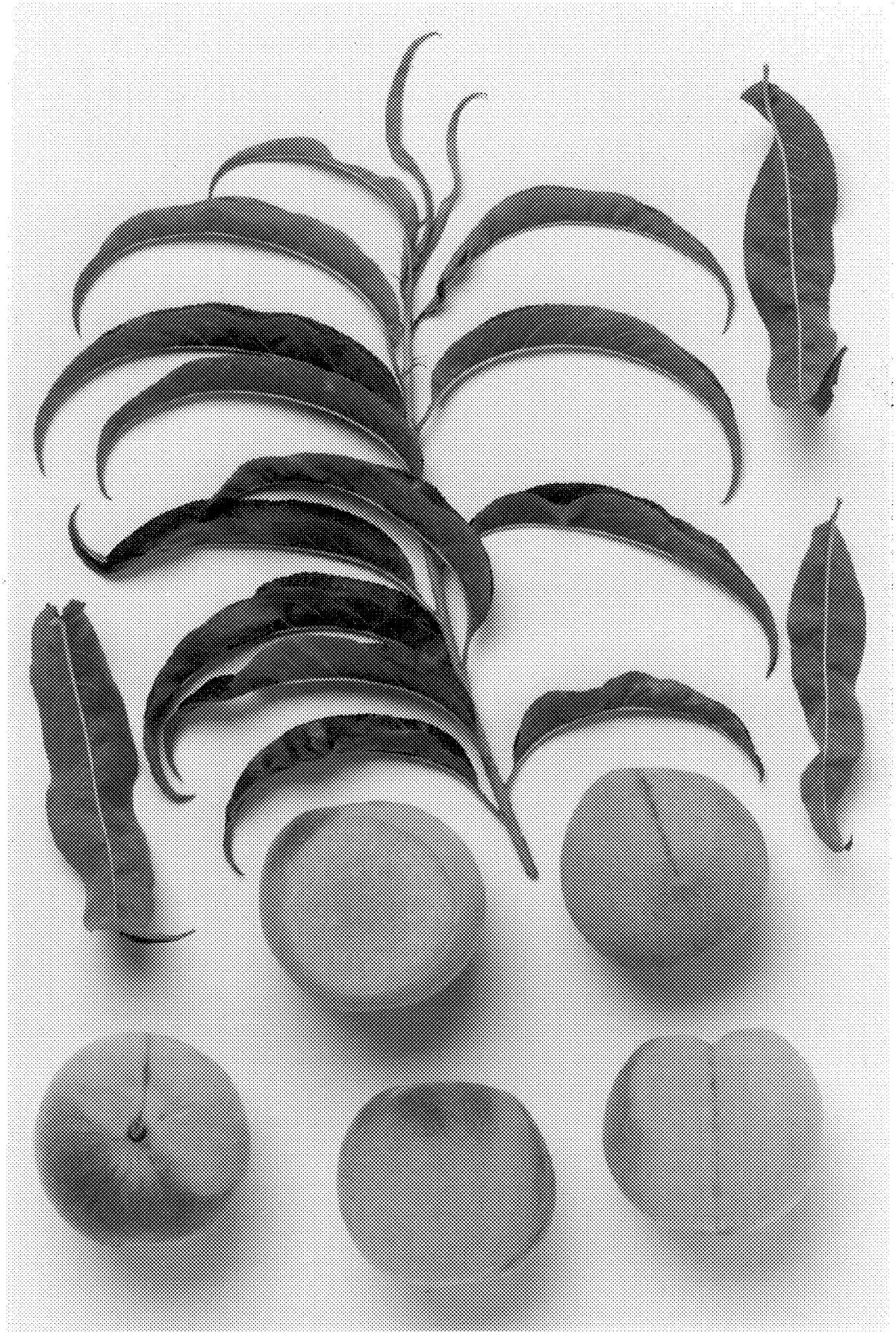

* * * * *